(12) United States Patent
Takano et al.

(10) Patent No.: US 10,508,171 B2
(45) Date of Patent: Dec. 17, 2019

(54) METHOD FOR PRODUCING PERFLUOROPOLYETHER ACYL FLUORIDE

(71) Applicant: DAIKIN INDUSTRIES, LTD., Osaka-shi, Osaka (JP)

(72) Inventors: Shinya Takano, Settsu (JP); Takashi Nomura, Settsu (JP); Kenichi Katsukawa, Settsu (JP); Masato Naitou, Settsu (JP)

(73) Assignee: DAIKIN INDUSTRIES, LTD., Osaka (JP)

( * ) Notice: Subject to any disclaimer, the term of this patent is extended or adjusted under 35 U.S.C. 154(b) by 94 days.

(21) Appl. No.: 15/562,184

(22) PCT Filed: Mar. 31, 2016

(86) PCT No.: PCT/JP2016/060806
§ 371 (c)(1),
(2) Date: Sep. 27, 2017

(87) PCT Pub. No.: WO2016/159302
PCT Pub. Date: Oct. 6, 2016

(65) Prior Publication Data
US 2018/0105645 A1    Apr. 19, 2018

(30) Foreign Application Priority Data
Mar. 31, 2015   (JP) .................... 2015-073630

(51) Int. Cl.
| | | |
|---|---|---|
| C08G 65/00 | (2006.01) | |
| B01J 23/42 | (2006.01) | |
| B01J 23/44 | (2006.01) | |
| B01J 23/46 | (2006.01) | |
| C07B 31/00 | (2006.01) | |
| C08G 65/332 | (2006.01) | |

(52) U.S. Cl.
CPC ............ C08G 65/007 (2013.01); B01J 23/42 (2013.01); B01J 23/44 (2013.01); B01J 23/462 (2013.01); B01J 23/464 (2013.01); C07B 31/00 (2013.01); C08G 65/3322 (2013.01); C08G 2650/48 (2013.01)

(58) Field of Classification Search
CPC ............. C08G 65/007; C08G 65/3322; C08G 2650/48; C07B 31/00; B01J 23/44; B01J 23/462; B01J 23/464; B01J 23/42
USPC ........................................................ 526/247
See application file for complete search history.

(56) References Cited

U.S. PATENT DOCUMENTS

| | | |
|---|---|---|
| 4,940,814 A | 7/1990 | Schwertfeger |
| 2004/0024153 A1 | 2/2004 | Di Meo et al. |
| 2004/0068144 A1* | 4/2004 | Meo .................... C08G 65/007 564/503 |
| 2010/0121106 A1 | 5/2010 | De Patto et al. |

FOREIGN PATENT DOCUMENTS

| | | |
|---|---|---|
| JP | 2004-067683 A | 3/2004 |
| JP | 2004-068007 A | 3/2004 |
| JP | 2005-075820 A | 3/2005 |
| JP | 2010-523617 A | 7/2010 |

OTHER PUBLICATIONS

Communication dated Jan. 21, 2019 from the European Patent Office in corresponding application No. 16773182.7.
Partial Supplementary European Search Report dated Oct. 18, 2018 issued by the European Patent Office in counterpart European application No. 16773182.7.
International Preliminary Report on Patentability dated Oct. 12, 2017 in counterpart international application No. PCT/JP2016/060806.
International Search Report for PCT/JP2016/060806 dated May 17, 2016.
Office Action dated Feb. 27, 2019 in counterpart CN Application No. 201680019802.

* cited by examiner

*Primary Examiner* — Hui H Chin
(74) *Attorney, Agent, or Firm* — Sughrue Mion, PLLC

(57) ABSTRACT

A process for producing a perfluoropolyether acyl fluoride which includes reducing a peroxyperfluoropolyether by using a formyl group-containing compound in the presence of a transition metal catalyst.

12 Claims, No Drawings

METHOD FOR PRODUCING PERFLUOROPOLYETHER ACYL FLUORIDE

CROSS REFERENCE TO RELATED APPLICATIONS

This application is a National Stage of International Application No. PCT/JP2016/060806 filed Mar. 31, 2016, claiming priority based on Japanese Patent Application No. 2015-073630 filed Mar. 31, 2015, the contents of all of which are incorporated herein by reference in their entirety.

TECHNICAL FIELD

The present invention relates to perfluoropolyether acyl fluoride.

BACKGROUND ART

A perfluoropolyether compound has excellent physical properties and is used in wide applications as a lubricant, a water and oil repellent, an antifouling agent, a release agent, or the like. In particular, a perfluoropolyether acyl fluoride is useful itself, and is also useful as an intermediate for the synthesis of various perfluoropolyether compounds. This perfluoropolyether acyl fluoride is known to be able to be prepared by reducing, for example, peroxyperfluoropolyether (that is, the perfluoropolyether compound containing —O—O—).

Conventionally, the reduction of the peroxyperfluoropolyether described above has been performed by contacting with hydrogen gas in the presence of a transition metal catalyst, for example, a transition metal catalyst carried on carbon (for example, Pd/C, etc.). This reduction reaction is shown in the following scheme 1.

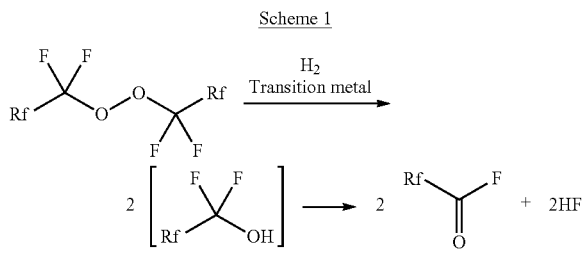

Scheme 1 wherein Rf is any perfluoro group.

As shown in the above scheme, in the reduction reaction, hydrogen fluoride is generated as a by-product. Since hydrogen fluoride poisons the catalyst, there is a problem that the catalyst activity decreases in the above method.

For the above problem, studies have been performed for maintains the catalyst activity for a long time even in the presence of hydrogen fluoride. As the catalyst, for example, Patent Document 1 discloses a transition metal (Pd, Pt, Rh, etc.) carried on a metal fluoride, and Patent Document 2 discloses a group VIII metal carried on a graphite-like material.

On the other hand, Patent Document 3 discloses that formic acid as a hydrogen donor in the reduction reaction of a carboxylic acid. However, for the reduction of peroxyperfluoropolyether, examples using the hydrogen donor have not been reported.

PRIOR ART DOCUMENT

Patent Document

Patent Document 1: JP 2004-67683 A
Patent Document 1: JP 2010-523617 A
Patent Document 1: JP 2005-75820 A

SUMMARY OF THE INVENTION

Problem to be Solved by the Invention

The transition metal carried on a metal fluoride described in Patent Document 1, and the a group VIII metal carried on a graphite-like material described in Patent Document 2 can maintain the catalyst activity for a certain period, but not be sufficient. In addition, since the reaction in Patent Documents 1 and 2 are batch reaction, there is a problem that the reaction must be performed under high pressure or a large excess of hydrogen gas is essential. When the continuous reaction (flow reaction) is used, there is a problem that a large excess of hydrogen gas is needed and the production cost is increased.

Therefore, an object of the present invention is to provide a process for the reduction of peroxyperfluoropolyether wherein the process is able to be efficiently performed under lower pressure, the catalyst activity is hardly decreased, and the production cost is low.

Means to Solve the Problem

As a result of intensively studying the above problems, the inventors of the present invention have found that by using a formyl group-containing compound as a hydrogen source but not hydrogen gas, the decrease of the catalyst activity is able to be suppressed and the reaction under lower pressure becomes possible, and the inventors reach the present invention.

According to the first aspect of the present invention, there is provided a process for producing perfluoropolyether acyl fluoride which comprises reducing peroxyperfluoropolyether by using a formyl group-containing compound in the presence of a transition metal catalyst.

According to the second aspect of the present invention, a process for producing a fluoropolyether acyl fluoride containing composition comprising fluoropolyether acyl fluoride having a $HCF_2$— group at its terminal of 0.01 to 5.00 mol % with respect to the whole of fluoropolyether acyl fluoride which comprises reducing peroxyperfluoropolyether by using a formyl group-containing compound in the presence of a transition metal catalyst.

According to the third aspect of the present invention, a fluoropolyether acyl fluoride containing composition comprising fluoropolyether acyl fluoride having a $HCF_2$— group at its terminal of 0.01 to 5.00 mol % with respect to the whole of fluoropolyether acyl fluoride.

Effect of the Invention

According to the present invention, by using the formyl group-containing compound as a hydrogen source, the poisoning of the catalyst by hydrogen fluoride is able to be suppressed and peroxyperfluoropolyether is able to be efficiently reduced.

EMBODIMENTS TO CARRY OUT THE INVENTION

Hereinafter, the process of the present invention will be described.

The process of the present invention is characterized by a process for producing a perfluoropolyether acyl fluoride which comprises reducing peroxyperfluoropolyether in the presence of a transition metal catalyst by using a formyl group-containing compound.

In the present invention, a "formyl group-containing compound" is a compound having a —CHO group.

In preferable embodiment, the formyl group-containing compound is formic acid or a formic acid derivative, more preferably formic acid.

The formic acid derivative is preferably formic acid ester or a formic acid salt. The formic acid ester is preferably methyl formate, ethyl formate, or propyl formate, more preferably methyl formate. The formic acid salt is preferably an alkali metal salt, or an ammonium salt, more preferably sodium formate or potassium formate.

The used amount of the formyl group-containing compound in the present invention can be determined depending on the used amount of peroxyperfluoropolyether and the content rate of —O—O— bonds. Since the formyl group-containing compound efficiently reduces peroxyperfluoropolyether, the large excess amount is not needed, for example, may be stoichiometric amount or slight excess amount to moles of —O—O— bonds.

The transition metal catalyst used in the present invention is not particularly limited. In the present invention, since the decrease of the catalyst activity is suppressed, the conventional transition metal catalyst such as Pd carried on carbon, or the like can be successfully used.

Examples of the transition metal used in the transition metal catalyst include, but are not particularly limited to, group VIII metals, for example, Pd, Pt, Rh, Ru, and the like, preferably Pd, Rh, Ru. The transition metal catalyst may be one or a mixture of two or more.

The used amount of the transition metal catalyst in the present invention is not particularly limited, but for example, 0.01 to 15% by mass, preferably 0.1 to 10.0% by mass, more preferably 1.0 to 10.0% by mass, for example, 1.0 to 5.0% by mass to peroxyperfluoropolyether.

The transition metal catalyst is preferably carried on a carrier. Examples of the carrier include, for example, carbon, alumina ($Al_2O_3$), a metal fluoride, a sulfate or a nitrate of an alkaline earth metal, a fibril, an ethylene diamine complex, polyethyleneimine, and the like.

As the carbon which is the carrier, various carbon carriers can be used, and an activated carbon, an amorphous carbon, graphite, diamond or the like can be used.

Examples of the metal fluoride include, for example, $CaF_2$, $SrF_2$, $BaF_2$, $MgF_2$, $AlF_3$, and the like.

Examples of the sulfate or the nitrate of an alkaline earth metal, for example, $CaSO_4$, $Ca(NO_2)_2$, $SrSO_4$, $Sr(NO_2)_2$, $BaSO_4$, $Ba(NO_2)_2$, and the like.

In view of ease of re-use and a cost, general carbon carrier such as an activated carbon, the sulfate or the nitrate of an alkaline earth metal are preferable. In view of size of the catalyst and resistance to hydrogen fluoride, a graphite or a metal fluoride is preferable.

The amount of the transition metal in the transition metal carrying catalyst used in the present invention is not particularly limited, but is preferably 0.1 to 10% by mass, more preferably 0.5 to 5% by mass with respect to transition metal carrying catalyst.

Peroxyperfluoropolyether which is able to be used in the process of the present invention is not limited as long as it is a perfluoropolyether compound having at least one —O—O— bond.

In one embodiment, the peroxyperfluoropolyether compound used in the present invention comprises the following structure (II).

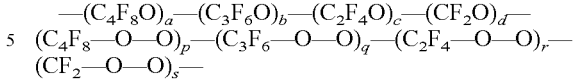

In the above formula, a, b, c, d, p, q, r and s are each independently 0 or an integer of 1 or more, and are not particularly limited as long as the sum of a, b, c and d is at least 1, and the sum of p, q, r and s is at least 1. Preferably, a, b, c, d, p, q, r and s are each independently an integer of 0 or more and 200 or less, for example, an integer of 1 or more and 200 or less, more preferably, each independently an integer of 0 or more and 100 or less, for example, an integer of 1 or more and 100 or less. The occurrence order of the respective repeating units in parentheses with the subscript a, b, c, d, p, q, r or s is not limited in the formula.

In one embodiment, a and b are each independently an integer of 0 or more and 30 or less, for example, 1 or more and 20 or less, and c and d are each independently an integer of 1 or more and 200 or less, preferably an integer of 5 or more and 200 or less, more preferably an integer of 10 or more and 200 or less, p and q are each independently an integer of 0 or more and 30 or less, for example, an integer of 1 or more and 20 or less, r and s are each independently an integer of 1 or more and 200 or less, preferably an integer of 5 or more and 200 or less, more preferably an integer of 10 or more and 200 or less.

Among these repeating units, the —($OC_4F_8$)— group may be any of —($OCF_2CF_2CF_2CF_2$)—, —($OCF(CF_3)CF_2CF_2$)—, —($OCF_2CF(CF_3)CF_2$)—, —($OCF_2CF_2CF(CF_3)$)—, —($OC(CF_3)_2CF_2$)—, —($OCF_2C(CF_3)_2$)—, —($OCF(CF_3)CF(CF_3)$)—, —($OCF(C_2F_5)CF_2$)— and —($OCF_2CF(C_2F_5)$)—, preferably —($OCF_2CF_2CF_2CF_2$)—. The —($OC_3F_6$)— group may be any of —($OCF_2CF_2CF_2$)—, —($OCF(CF_3)CF_2$)— and —($OCF_2CF(CF_3)$)—, preferably —($OCF_2CF_2CF_2$)—. The —($OC_2F_4$)—group may be any of —($OCF_2CF_2$)— and —($OCF(CF_3)$)—, preferably —($OCF_2CF_2$)—.

In one embodiment, the peroxyperfluoropolyether compound comprises the structure of

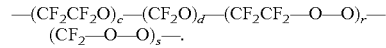

In another embodiment, the peroxyperfluoropolyether compound comprises the structure of

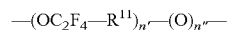

wherein $R^{11}$ is a group selected from $OC_2F_4$, $OC_3F_6$ and $OC_4F_8$, or a combination of two or three groups selected from these groups, n' is an integer of 2 to 100, preferably an integer of 2 to 50, n" is an integer of 1 to 50, preferably an integer of 2 to 30, more preferably an integer of 2 to 10, and the occurrence order of the respective repeating units in parentheses with the subscript n' or n' is not limited in the formula. The combination of two or more independently selected from $OC_2F_4$, $OC_3F_6$ and $OC_4F_8$ include, but are not particular limited to, for example, —$OC_2F_4OC_3F_6$—, —$OC_2F_4OC_4F_8$—, —$OC_3F_6OC_2F_4$—, —$OC_3F_6OC_3F_6$—, —$OC_3F_6OC_4F_8$—, —$OC_4F_8OC_4F_8$—, —$OC_4F_8OC_3F_6$—, —$OC_4F_8OC_2F_4$—, —$OC_2F_4OC_2F_4OC_3F_6$—, —$OC_2F_4OC_2F_4OC_4F_8$—, —$OC_2F_4OC_3F_6OC_2F_4$—, —$OC_2F_4OC_3F_6OC_3F_6$—, —$OC_2F_4OC_4F_8OC_2F_4$—, —$OC_3F_6OC_2F_4OC_2F_4$—, —$OC_3F_6OC_2F_4OC_3F_6$—, —OC₃F₆OC₃F₆OC₂F₄—, —OC₄F₈OC₂F₄OC₂F₄—, and the like. In the above formula, OC₂F₄, OC₃F₆ and OC₄F₈ may be straight or branched, preferably straight.

In one embodiment, the terminal group of the peroxyperfluoropolyether compound may be —(CF₂)₁-R⁵. In the formula, R⁵ is —F, —COF, —CF₃₋ₘClₘ, m is an integer of 1 to 3, 1 is an integer of 0 to 4, for example, an integer of 1 to 4. It is noted that when 1 is 0, R⁵ is directly attached to the perfluoropolyether structure.

The peroxyperfluoropolyether compound can be prepared for example, by polymerizing tetrafluoroethylene or hexafluoropropene in the presence of oxygen, although it is not particularly limited thereto. The reaction is described, for example, in U.S. Pat. Nos. 3,442,942, 3,650,928, or U.S. Pat. No. 3,665,041.

The content ratio of the —O—O— bond in the peroxyperfluoropolyether may be represented by the oxidizing power (PO).

PO means grams of activity oxygen per 100 g of peroxyperfluoropolyether. The grams of activity oxygen can be measured by the well-known method, in particular, an oxidation-reduction titration (for example, an oxidation-reduction titration with thiosulfate) or ¹⁹F-NMR.

In the present invention, the PO value may be 0.1 to 5.0, preferably 0.3 to 2.0, more preferably 0.5 to 1.0.

A number average molecular weight of peroxyperfluoropolyether used in the present invention is not particularly limited, but may be for example, 200 to 100,000, preferably 1,000 to 50,000, more preferably 2,000 to 30,000, further preferably 3,000 to 20,000.

A reaction temperature in the present invention is not particularly limited, but may be, for example, 15° C. to 200° C., preferably 50° C. to 150° C., more preferably 80° C. to 150° C.

A reaction pressure in the present invention is not particularly limited, but may be, for example, 1 to 10 atoms, preferably 1 to 5 atoms, more preferably 1 to 3 atoms.

In one embodiment, the reaction of the present invention is performed in a solvent. As the solvent, as long as it does not adversely detrimental to the reaction, any solvents can be used. The solvent is preferably a non-aqueous solvent, more preferably a non-aqueous solvent CFC-11, CFC-113, HCFC-123, HCFC-225, FC-41-12, FC-51-14, or the like. By using the non-aqueous solvent, the hydrolysis of the produced perfluoropolyether acyl fluoride to a carboxylic acid can be suppressed.

In another embodiment, the process of the present invention is performed in a solvent-free condition, that is, without using a solvent. In this case, the formyl group-containing compound may function as a solvent. By performing the reaction in a solvent-free condition, the hydrolysis of the produced perfluoropolyether acyl fluoride to a carboxylic acid can be suppressed.

The reduction of peroxyperfluoropolyether provides perfluoropolyether acyl fluoride.

In one embodiment, the perfluoropolyether acyl fluoride obtained by the reduction reaction of the present invention is represented by the following formula (I):

X—(C₄F₈O)ₐ—(C₃F₆O)ᵦ—(C₂F₄O)ᵧ—(CF₂O)ₐ—Y wherein:

a, b, c and d are each independently 0 or an integer of 1 or more, preferably an integer of 0 or more and 200 or less, for example, an integer of 1 or more and 200 or less, more preferably an integer of 0 or more and 100 or less, for example, an integer of 1 or more and 100 or less, the sum of a, b, c and d is at least 1, and the occurrence order of the respective repeating units in parentheses with the subscript a, b, c or d is not limited in the formula, X is —R⁵, R⁵ is —F, —COF, —CF₃₋ₙClₙ, m is an integer of 1-3, Y is —(CF₂)ₙ—COF, and n is an integer of 0-3, for example, an integer of 1-3.

In preferable embodiment, a and b are each independently an integer of 0 or more and 30 or less, for example, 1 or more and 20 or less, c and d are each independently an integer of 1 or more and 200 or less, preferably an integer of 5 or more and 200 or less, more preferably an integer of 10 or more and 200 or less, and the occurrence order of the respective repeating units in parentheses with the subscript a, b, c or d is not limited in the formula.

The molecular weight of the perfluoropolyether acyl fluoride may be, for example, 100 to 100,000, preferably 500 to 30,000, more preferably 2,000 to 20,000, further preferably 3,000 to 20,000.

In one embodiment, the reduction reaction described above may be performed in the presence of an agent for preventing decrease of catalyst activity.

The "agent for preventing decrease of catalyst activity" in the present invention means a compound suppressing the decrease of the catalyst activity, and includes, for example, a compound trapping hydrogen fluoride poisoning a catalyst, a compound inhibiting a contact between a catalyst and hydrogen fluoride, and the like.

The amount of the agent for preventing decrease of catalyst activity used in the present invention is not particularly limited, but may be preferably 1 to 50% by mass, more preferably 5 to 20% by mass with respect to peroxyperfluoropolyether.

In preferable embodiment, the agent for preventing decrease of catalyst activity is an orthoester, sodium fluoride, or potassium fluoride, preferably an orthoester.

Examples of the orthoester include a compound of the following formula:

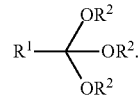

In the above formula, R¹ is a hydrogen atom or an alkyl group having 1-6 carbons. The alkyl group having 1-6 carbons is preferably alkyl group having 1-3 carbons, more preferably a methyl group.

R² is each independently an alkyl group having 1-6 carbons, preferably an alkyl group having 1-3 carbons, more preferably a methyl group.

In preferable embodiment, R¹ is a hydrogen atom, that is, the orthoester is trialkyl formate.

In further preferable embodiment, R¹ is a hydrogen atom, and R² is a methyl group, that is, the orthoester is orthotrimethyl formate.

While the present invention is not bound by any theory, a mechanism that the orthoester suppresses the poisoning by hydrogen fluoride is considered as follows. The orthoester is reacted with hydrogen fluoride generated in the reduction reaction of the peroxyperfluoropolyether and consumes hydrogen fluoride, thereby suppressing the poisoning by hydrogen fluoride. The reaction of the orthoester and hydrogen fluoride is considered to occur as shown in the following scheme 2.

Scheme 2

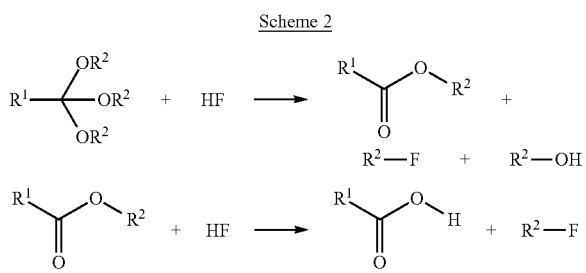

In addition, it may be considered that since hydrogen fluoride has a higher solubility in the orthoester phase, hydrogen fluoride is eliminated from fluorous phase, a contact of hydrogen fluoride and a catalyst is inhibited, and poisoning of the catalyst is suppressed.

It may be considered that sodium fluoride and potassium fluoride adsorb hydrogen fluoride, thereby suppressing the poisoning of the catalyst. In view of deliquescence, sodium fluoride is more preferable.

By treating the perfluoropolyether acyl fluoride obtained by the process described above with an alkyl source compound such as alcohol or orthoester, or the like, it is possible to convert the perfluoropolyether acyl fluoride to the perfluoropolyetheralkyl ester.

In preferable embodiment, by using orthoester as an agent for preventing decrease of catalyst activity, the reduction reaction and the esterification can be performed simultaneously. In this case, the perfluoropolyether acyl fluoride obtained by the reduction reaction is reacted with the orthoester present in the system and/or an alcohol generated as a result that the orthoester traps hydrogen fluoride to provide the perfluoropolyetheralkyl ester.

In one embodiment, the perfluoropolyetheralkyl ester obtained by the process of the present invention is represented by the following formula:

$$X'—(C_4F_8O)_a—(C_3F_6O)_b—(C_2F_4O)_c—(CF_2O)_d—Y'$$

wherein:

a, b, c and d are each independently 0 or an integer of 1 or more, preferably an integer of 0 or more and 200 or less, for example, 1 or more and 200 or less, more preferably an integer of 0 or more and 100 or less, for example, an integer of 1 or more and 100 or less, the sum of a, b, c and d is at least 1, and the occurrence order of the respective repeating units in parentheses with the subscript a, b, c or d is not limited in the formula.

X' is $—R_5$, $R^5$ is $—F$, $—COOR^2$, $—CF_{3-m}Cl_m$, m is an integer of 1-3, Y' is $—(CF_2)_n—COOR^2$, n is an integer of 0-3, for example, an integer of 1-3, and $R^2$ is each independently hydrogen atom or an alkyl group having 1-6 carbon atoms.

In preferable embodiment, a and b are each independently an integer of 0 or more and 30 or less, for example, 1 or more and 20 or less, c and d are each independently an integer of 1 or more and 200 or less, preferably 5 or more and 200 or less, more preferably 10 or more and 200 or less, and the occurrence order of the respective repeating units in parentheses with the subscript a, b, c or d is not limited in the formula.

In the process of the present invention, since a formyl group-containing compound is used as a hydrogen source, the poisoning by hydrogen fluoride is suppressed. In addition, since the reaction can be reacted under a lower pressure condition as compared with the case of using a hydrogen gas, the safety of the reaction is increased. In addition, since it becomes easy to remove hydrogen fluoride generated in the system, the poisoning of the catalyst can be more suppressed. In addition, since the formyl group-containing compound can efficiently reduce the peroxyperfluoropolyether even in a continuous reaction, a large excess amount is not needed, and the production cost can be suppressed in comparison with the case of using hydrogen gas.

In the process of the present invention, a composition comprising the perfluoropolyether acyl fluoride is obtained. The composition can contain a fluoropolyether acyl fluoride having a $HCF_2$— group. That is, when the perfluoropolyether acyl fluoride is produced by using the process of the present invention, a composition comprising fluoropolyether acyl fluoride having a $HCF_2$— group.

Therefore, the present invention provides a process for producing a fluoropolyether acyl fluoride containing composition comprising fluoropolyether acyl fluoride having a $HCF_2$— group at its terminal of 0.01 to 5.00 mol % with respect to the whole of fluoropolyether acyl fluoride which comprises reducing peroxyperfluoropolyether by using a formyl group-containing compound in the presence of a transition metal catalyst.

The fluoropolyether acyl fluoride having a $HCF_2$— group at its terminal may be preferably a fluoropolyether acyl fluoride of the following formula (III):

$$X''—(C_4F_8O)_a—(C_3F_6O)_b—(C_2F_4O)_c—(CF_2O)_d—Y$$

wherein:

a and b are each independently an integer of 0 or more and 30 or less, c and d are each independently an integer of 1 or more and 200 or less, occurrence order of the respective repeating units in parentheses with the subscript a, b, c or d is not limited in the formula, X" is $—R^6$, $R^6$ is $—CHF_2$, m is an integer of 1-3, Y is $—(CF_2)—COF$, and n is an integer of 0-3.

The content of the fluoropolyether acyl fluoride having a $HCF_2$— group may be preferably 0.01 to 4.00 mol %, for example, 0.10 to 3.50 mol % or 0.30 to 2.00 mol % with respect to the whole of the fluoropolyether acyl fluoride.

The content of the fluoropolyether acyl fluoride having a $HCF_2$— group in the composition can be adjusted by changing a concentration of a formyl group-containing compound used.

By reacting the fluoropolyether acyl fluoride having a $HCF_2$— group with a base, it becomes possible to introduce an optional functional group. Since the fluoropolyether acyl fluoride containing composition obtained by the process of the present invention contains the fluoropolyether acyl fluoride having a $HCF_2$— group of a few percent, the fluoropolyether acyl fluoride in the composition can be modified at the terminal at a few percent.

Therefore, the present invention also provides a fluoropolyether acyl fluoride containing composition wherein the fluoropolyether acyl fluoride having a $HCF_2$— group is contained at 0.01 to 5.00 mol % with respect to the whole of the fluoropolyether acyl fluoride in the composition.

In one embodiment, the fluoropolyether acyl fluoride containing composition can be obtained by using the process of the present invention.

The fluoropolyether acyl fluoride other than the fluoropolyether acyl fluoride having a $HCF_2$— group contained in the composition may be mainly the perfluoropolyether acyl fluoride of X—$(C_4F_8O)_a$—$(C_3F_6O)_b$—$(C_2F_4O)_c$—$(CF_2O)_d$—Y. The content of the perfluoropolyether acyl fluoride may be preferably 90 to 99.9 mol %.

Examples of the other fluoropolyether acyl fluoride include a perfluoropolyether acyl fluoride having a carboxyl group (—COOH) at its terminal. The content of the perfluoropolyether acyl fluoride may be preferably 0 to 7.0 mol %, more preferably 1.0 to 7.0 mol %.

Hereinbefore, although the process of the present invention is described in detail, the present invention is not limited to the above and can be modified without departing from the scope of the present invention.

EXAMPLES

Example 1

Peroxyperfluoropolyether (100 g, number average molecular weight=15,600, PO=0.83), a Pd/C catalyst (2.45 g, manufactured by N.E. CHEMCAT CORPORATION, containing 5 wt % of Pd to weight of the catalyst) and formic acid (16.40 g) were added to an autoclave.

Nitrogen gas was introduced at the rate of 10 mL/min, stirring was performed under the pressure of 0.2 MPa, at 120° C. for 12 hours, and then the autoclave was opened. The resulting reaction solution was filtered and the volatiles were distilled off. As a result, the desired perfluoropolyether acyl fluoride containing material (78.78 g) was obtained.

The resulting perfluoropolyether acyl fluoride containing material was analyzed by $^{19}$F-NMR, as a result of which, no fluorine substituent adjacent to a peroxy bond (—O—O—) was observed, and the acyl fluoride terminal was 93.6%, the carboxylic acid terminal was 2.2%, and the —$CHF_2$ terminal was 4.2%. Therefore, it was confirmed that the peroxyperfluoropolyether was converted to a perfluoropolyether acyl fluoride at the high conversion.

Example 2

Peroxyperfluoropolyether (50 g, number average molecular weight=15,600, PO=0.83), a Pd/C catalyst (1.05 g, manufactured by N.E. CHEMCAT CORPORATION, containing 5 wt % of Pd to weight of the catalyst) and formic acid (8.20 g) were added to a glass reactor.

Nitrogen gas was bubbled at the rate of 10 mL/min, and stirring was performed at 120° C. for 6 hours. Then, the resulting reaction solution was filtered and the volatiles were distilled off. As a result, the desired perfluoropolyether acyl fluoride containing material (39.27 g) was obtained.

The resulting polyfluoropolyether acyl fluoride containing material was analyzed by $^{19}$F-NMR, as a result of which, no fluorine substituent adjacent to a peroxy bond (—O—O—) was observed, and the acyl fluoride terminal was 94.5%, the carboxylic acid terminal was 2.1%, and the —$CHF_2$ terminal was 3.4%.

Example 3

Peroxyperfluoropolyether (50 g, number average molecular weight=15,600, PO=0.83), a Pd/C catalyst (3.55 g, manufactured by N.E. CHEMCAT CORPORATION, containing 1.5 wt % of Pd to weight of the catalyst) and formic acid (8.20 g) were added to a glass reactor.

After stirring at 120° C. for 3 hours, the resulting reaction solution was filtered and the volatiles were distilled off. As a result, the desired perfluoropolyether acyl fluoride containing material (38.72 g) was obtained.

The resulting polyfluoropolyether acyl fluoride containing material was analyzed by $^{19}$F-NMR, as a result of which, no fluorine substituent adjacent to a peroxy bond (—O—O—) was observed, and the acyl fluoride terminal was 95.3%, the carboxylic acid terminal was 4.3%, and the —$CHF_2$ terminal was 0.4%.

Example 4

Peroxyperfluoropolyether (50 g, number average molecular weight=14,800, PO=0.69), a Pd/C catalyst(0.91 g, manufactured by N.E. CHEMCAT CORPORATION, containing 5 wt % of Pd to weight of the catalyst) were added to a glass reactor.

After heating the reaction solution to 120° C., formic acid (3.55 g) was added, further stirring was performed at 120° C. for 3 hours. Then, the resulting reaction solution was filtered and the volatiles were distilled off. As a result, the desired perfluoropolyether acyl fluoride containing material (39.89 g) was obtained.

The resulting polyfluoropolyether acyl fluoride containing material was analyzed by $^{19}$F-NMR, as a result of which, no fluorine substituent adjacent to a peroxy bond (—O—O—) was observed, and the acyl fluoride terminal was 93.9%, the carboxylic acid terminal was 5.7%, and the —$CHF_2$ terminal was 0.4%.

Comparative Example 1

Peroxyperfluoropolyether (50 g, number average molecular weight=15,600, PO=0.83), a Pd/C catalyst(1.05 g, manufactured by N.E. CHEMCAT CORPORATION, containing 5 wt % of Pd to weight of the catalyst) were added to a glass reactor.

Nitrogen gas was bubbled at the rate of 10 mL/min, and stirring was performed at 120° C. for 6 hours. Then, the resulting reaction solution was filtered and the volatiles were distilled off. As a result, the desired perfluoropolyether acyl fluoride containing material was obtained.

The resulting polyfluoropolyether acyl fluoride containing material was analyzed by $^{19}$F-NMR, as a result of which, a signal of the fluorine substituent adjacent to a peroxy bond (—O—O—) was observed, and the reaction conversion was 60.3%.

INDUSTRIAL APPLICABILITY

The present invention is suitably used in producing a perfluoropolyether acyl fluoride compound.

The invention claimed is:

1. A process for producing a perfluoropolyether acyl fluoride which comprises reducing a peroxyperfluoropolyether with a formyl group-containing compound in the presence of a transition metal catalyst, wherein the formyl group-containing compound is formic acid or formic acid derivatives.

2. The process according to claim 1 wherein the perfluoropolyether acyl fluoride is a compound of the following formula (I):

$$X-(C_4F_8O)_a-(C_3F_6O)_b-(C_2F_4O)_c-(CF_2O)_d-Y$$

wherein:
   a, b, c and d are each independently 0 or an integer of 1 or more, the sum of a, b, c and d is at least 1, and the occurrence order of the respective repeating units in parentheses with the subscript a, b, c or d is not limited in the formula,
   X is $-R^5$,
   $R^5$ is $-F$, $-COF$, $-CF_{3-m}Cl_m$,
   m is an integer of 1-3,
   Y is $-(CF_2)_n-COF$, and
   n is an integer of 0-3.

3. The process according to claim 1 wherein perfluoropolyether acyl fluoride is a compound of the following formula (I'):

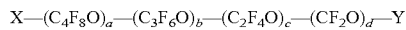

$$X-(C_4F_8O)_a-(C_3F_6O)_b-(C_2F_4O)_c-(CF_2O)_d-Y$$

wherein:
   a and b are each independently 0 or more and 30 or less,
   c and d are each independently 1 or more and 200 or less, and
   the occurrence order of the respective repeating units in parentheses with the subscript a, b, c or d is not limited in the formula,
   X is $-R^5$,
   $R^5$ is $-F$, $-COF$, $-CF_{3-m}Cl_m$,
   m is an integer of 1-3,
   Y is $-(CF_2)_n-COF$, and
   n is an integer of 0-3.

4. The process according to claim 1 wherein the formyl group-containing compound is formic acid.

5. The process according to claim 1 wherein the peroxyperfluoropolyether compound comprises the following structure (II):

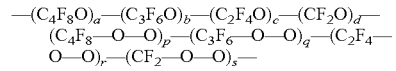

$$-(C_4F_8O)_a-(C_3F_6O)_b-(C_2F_4O)_c-(CF_2O)_d-$$
$$(C_4F_8-O-O)_p-(C_3F_6-O-O)_q-(C_2F_4-O-O)_r-(CF_2-O-O)_s-$$

wherein:
   a, b, c, d, p, q, r and s are each independently 0 or an integer of 1 or more, the sum of a, b, c and d is at least 1, and the sum of p, q, r and s is at least 1, and
   the occurrence order of the respective repeating units in parentheses with the subscript a, b, c, d, p, q, r or s is not limited in the formula.

6. The process according to claim 1 wherein the transition metal is selected form Pd, Pt, Rh, Ru and a mixture thereof.

7. The process according to claim 1 wherein the used amount of the transition metal catalyst is in the range of 0.1 to 10.0% by mass with respect to peroxyperfluoropolyether.

8. The process according to claim 1 wherein the used amount of the transition metal catalyst is in the range of 1.0 to 10.0% by mass with respect to peroxyperfluoropolyether.

9. The process according to claim 1 wherein the reaction temperature is 50 to 200° C.

10. The process according to claim 1 wherein the reaction temperature is 50 to 150° C.

11. The process according to claim 1 which is performed in a solvent-free condition.

12. The process according to claim 1 which is performed in a non-aqueous solvent.

\* \* \* \* \*